United States Patent
Voliani

(10) Patent No.: US 11,253,615 B2
(45) Date of Patent: Feb. 22, 2022

(54) PROCESS FOR THE PREPARATION OF HOLLOW NANOPARTICLES WITH A METAL CORE

(71) Applicant: FONDAZIONE ISTITUTO ITALIANO DI TECNOLOGIA, Genoa (IT)

(72) Inventor: Valerio Voliani, Leghorn (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 75 days.

(21) Appl. No.: 16/099,715

(22) PCT Filed: May 10, 2017

(86) PCT No.: PCT/IB2017/052723
§ 371 (c)(1),
(2) Date: Nov. 8, 2018

(87) PCT Pub. No.: WO2017/195127
PCT Pub. Date: Nov. 16, 2017

(65) Prior Publication Data
US 2019/0151482 A1   May 23, 2019

(30) Foreign Application Priority Data
May 13, 2016   (IT) .................. 102016000049532

(51) Int. Cl.
| | | |
|---|---|---|
| *A61K 49/18* | (2006.01) | |
| *A61K 41/00* | (2020.01) | |
| *B22F 1/00* | (2006.01) | |
| *B22F 1/02* | (2006.01) | |
| *C01B 33/18* | (2006.01) | |
| *B22F 9/24* | (2006.01) | |
| *A61K 49/22* | (2006.01) | |
| *F02M 51/00* | (2006.01) | |
| *H01F 5/04* | (2006.01) | |
| *H01F 7/06* | (2006.01) | |
| *H01F 41/10* | (2006.01) | |
| *H01R 4/14* | (2006.01) | |
| *B82Y 5/00* | (2011.01) | |
| *B82Y 40/00* | (2011.01) | |

(52) U.S. Cl.
CPC ........ *A61K 49/183* (2013.01); *A61K 41/0038* (2013.01); *A61K 49/1866* (2013.01); *A61K 49/225* (2013.01); *B22F 1/0018* (2013.01); *B22F 1/02* (2013.01); *B22F 9/24* (2013.01); *C01B 33/18* (2013.01); *F02M 51/005* (2013.01); *H01F 5/04* (2013.01); *H01F 7/06* (2013.01); *H01F 41/10* (2013.01); *B82Y 5/00* (2013.01); *B82Y 40/00* (2013.01); *C01P 2002/84* (2013.01); *C01P 2004/04* (2013.01); *C01P 2004/34* (2013.01); *C01P 2004/64* (2013.01); *H01F 2007/062* (2013.01); *H01R 4/14* (2013.01)

(58) Field of Classification Search
CPC ................ A61K 49/183; A61K 49/225; A61K 41/0038; A61K 49/1866; F02M 51/005; H01F 5/04; H01F 7/06; H01F 41/10; B22F 9/24; B22F 1/0018; B22F 1/02; C01B 33/18; H01R 4/14; B82Y 5/00; B82Y 40/00; C01P 2002/84; C01P 2004/04; C01P 2004/34; C01P 2004/64
See application file for complete search history.

(56) References Cited

U.S. PATENT DOCUMENTS

| | | | |
|---|---|---|---|
| 2003/0147966 A1* | 8/2003 | Franzen | A61K 49/0047 424/491 |
| 2011/0269148 A1* | 11/2011 | Huang | G01N 33/54313 435/7.1 |
| 2014/0221199 A1 | 8/2014 | Devi et al. | |

FOREIGN PATENT DOCUMENTS

CN         102019431 A         4/2011

OTHER PUBLICATIONS

Li et al. (CN102672195A Translation) (Year: 2012).*
Bommel et al.,"Poly (L-lysine) Aggregates as Templates for the Formation of Hollow Silica Spheres", Advanced Materials, 2001, vol. 13, No. 19, pp. 1472-1476.
Freitag et al., "Preparation and characterization of multicore SERS labels by controlled aggregation of gold nanoparticles", Vibrational Spectroscopy, 2012, vol. 60, pp. 79-84.
Luo et al., "From Aggregation-Induced Emission of Au(I)-Thiolate Complexes to Ultrabright Au(O)@Au(I)-Thiolate Core-Shell Nanoclusters". Journal of the American Chemical Society, 2012, vol. 134, No. 40, pp. 16662-16670.
Wu et al., "Multifunctional spherical gold nanocluster aggregate@polyacrylic acid@mesoporous silica nanoparticles for combined cancer dual-modal imaging and chemo-therapy", Journal of Materials Chemistry B, 2015, vol. 3, No. 12, pp. 2421-2425.
Yin et al., "A general and feasible method for the fabrication of functional nanoparticles in mesoporous silica hollow composite spheres", Journal of Materials Chemistry, 2012, vol. 22, No. 22, pp. 11245-11251.

(Continued)

Primary Examiner — Quanglong N Truong
(74) Attorney, Agent, or Firm — Lucas & Mercanti, LLP

(57) ABSTRACT

The present invention relates to silica hollow nanoparticles having inside their cavity a metal core consisting of inorganic nanostructures coated by a protective agent and agglomerated with a polymeric aggregating agent, useful in particular in medicine in the bio-imaging techniques and/or in the radio-therapeutic or chemo-therapeutic techniques; the invention moreover refers to a process for the preparation of such nanoparticles.

17 Claims, 1 Drawing Sheet

(56) References Cited

OTHER PUBLICATIONS

International Search Report and Written Opinion for Corresponding International Application No. PCT/IB2016/051168 (dated May 9, 2016) (11 Pages).
Cassano et al., "Biodegradable hollow silica nanospheres containing gold nanoparticle arrays", ChemComm, 2015, vol. 51, No. 49, pp. 9939-9941.
Wang et al., "Yolk-Shell Catalyst of Single Au Nanoparticle Encapsulated within Hollow Mesoporous Silica Microspheres", ACS Catal., 2011, vol. 1, No. 3, pp. 207-211.
Wang et al., "Synthesis and self-assembly of silica-coated anisotropic gold nanoparticle films", Nanotechnology, 2006, vol. 17, No. 8, pp. 1819-1824.
International Search Report and Written Opinion for Corresponding international Application No. PCT/IB2017/052723 (dated Sep. 5, 2017) (12 Pages).

\* cited by examiner

PROCESS FOR THE PREPARATION OF HOLLOW NANOPARTICLES WITH A METAL CORE

CROSS-REFERENCE TO RELATED APPLICATIONS

This application is a 371 of PCT/IB2017/052723, filed May 10, 2017, which claims the benefit of Italian Patent Application No. 102016000049532, filed May 13, 2016.

FIELD OF THE INVENTION

The present invention relates in general to the field of nanomaterials, and more precisely it relates to a novel process for the synthesis of hollow nanoparticles having a metal core and to such nanoparticles, useful in particular in medicine as therapeutic agents or in the bio-imaging techniques.

STATE OF THE ART

The unexpected properties of metallic nanoparticles have made it possible in recent years to create innovative, highly effective and personalized therapeutic and diagnostic agents. Examples are the numerous nanostructures proposed as contrast media for the visualization of in vivo tissues or organs, for the targeted transport of molecules within the cells, or for therapies based on photothermic effects or on effects of X-rays increase.

Despite their intriguing qualities and high expectations, no noble metal nanoparticles were able to be transposed from animal models to the actual use in humans. In fact, in order to make this use possible in humans, it is necessary that nanoparticles, after carrying out their diagnostic or therapeutic action in a human organism, be completely eliminated within a reasonable period of time. This requirement has been historically fixed by the US Food and Drug Administration for every type of chemotherapeutic agent, and it is now standardized.

The most efficient pathway for the elimination of the agents injected in the human body is recognized to be that of renal excretion, which is controlled by the filtration through kidney glomeruli and has shown a threshold value in the size of the particles to be ejected of maximum 8 nm. Larger objects can be eliminated through other routes of excretion of the human body, that is through the liver, or the spleen, respectively in the bile and the faeces. The elimination pathway through the liver is particularly suitable for capturing and eliminating biological material with a hydrodynamic diameter of 10-20 nm, such as viruses. The excretion path through the spleen, on the other hand, is formed by intra-endothelial fissures in the venous sinus, with dimensions of the fissures of the order of 200 nm, through which theoretically it would be possible to eliminate particles larger than the 8 nm mentioned above. Unfortunately, the excretion of injected metal nanoparticles through these routes has proved to be an extremely slow and inefficient process, causing accumulation of metals in the organisms and thus increasing the likelihood of long-term toxicity. Hence the need for the above-mentioned stringent requirement for the size of the nanoparticles injectable in the human body, recognized at a maximum of 8 nm.

Another disadvantage to be considered in the biomedical use of metallic nanoparticles, if retained in the body, is their possible interaction and/or interference with diagnostic techniques commonly used in medicine, such as the radiological techniques. For example, a radiological examination could be particularly susceptible to metals having a high atomic number accumulated in the patient's organs so that metals would interfere with the X-ray image due to changes in the linear attenuation coefficients. Another example is magnetic resonance, where the spaces without protons created by the accumulation of metals having high atomic number would cause significant interference, or still an ultrasound examination would result in an increased echogenicity, or a positron emission tomographic examination (PET) would be affected by photon attenuation (see, for example, *Pharmacol. Rev.* 53: 283-318, 2001). It is therefore indispensable, also to avoid interference with other commonly used diagnostic techniques, that the metal nanoparticles injected into a human body be completely excreted after having performed their function.

In addition, if the size of the metal nanoparticles used is below 3 nm, their chemical, physical and physiological properties might be altered or even lost. For example, gold nanoparticles having dimensions smaller than 2 nm in diameter lose their characteristic plasmonic resonance and, due to the high ratio surface/volume, the surface activities may also compromise the potential applications of these nanoparticles. In addition, their excretion from the body is so fast as to render impossible the required accumulation in a tissue, such as in the case of a tumour. Therefore, more than just having available ultra-small metallic nanoparticles, there is a need in the field for this kind of particles that also have good chemical and physical properties for their possible applications, particularly for biomedical applications, where it is moreover crucial the biodegradability of the nanoparticles.

Cassano D. et al., *Chem. Commun.*, 2015, 51, 9939-9941 disclose hollow silica nanospheres containing arrays of gold nanoparticles.

In view of what said above, it is evident that it is of fundamental importance to have available a process suitable for the preparation of metallic nanoparticles having the above-mentioned characteristics and particularly suitable for biomedical use. On the other hand, as far as is known to the Applicant, a process of preparation of metallic nanoparticles, which is reproducible and capable of controlling the size of the nanoparticles obtained, has not yet developed to date, for obtaining nanoparticles with useful characteristics for therapeutic and/or diagnostic purposes that can be eliminated through the kidneys pathway. As stated above, the need for such a process of preparation is still very much felt.

SUMMARY OF THE INVENTION

Now the Applicant has found a novel process of preparation of hollow silica nanoparticles, having in their cavity a metal core comprising inorganic hydrophilic nanostructures, protected by a suitable coating and agglomerated among each other thanks to a suitable polymeric aggregating agent.

This process allows preparing nanoparticles having well defined size and characteristics, moreover able to interact as a single body of suitable size with cells and tissues when they are used for instance in the bioimaging techniques, but also to be then biodegraded very rapidly into their own components so that they are not retained for a long time in the human body, but they are excreted quickly through the renal pathways. Furthermore, this process of preparation allows inserting ultra-small structures of magnetic nature inside the hollow nanoparticles, further broadening the field of the possible applications of the nanoparticles with a metal core, as described in details in the following.

It is therefore subject of the invention a process for the preparation of hollow silica nanoparticles, having a diameter smaller than 100 nm and a metal core inside the cavity comprising hydrophilic inorganic nanostructures, each of them having a diameter smaller than 3 nm and forming together an aggregate, the essential characteristics of this process being defined in the first of the attached claims.

A further subject of the present invention is represented by an intermediate in the above said process of preparation, as defined in the claim 10 here attached.

Silica hollow nanoparticles having diameter smaller than 100 nm, obtainable by the above said process and having in their cavity an aggregate of hydrophilic inorganic nanostructures each having size smaller than 3 nm, as defined in the claim 12 here attached, and their use as diagnostic and/or therapeutic agents, represent still a further subject of the invention.

Further important features of the preparation process of the invention and of the nanoparticles obtained by this process are illustrated in the following detailed description.

DETAILED DESCRIPTION OF THE INVENTION

Figure 1:
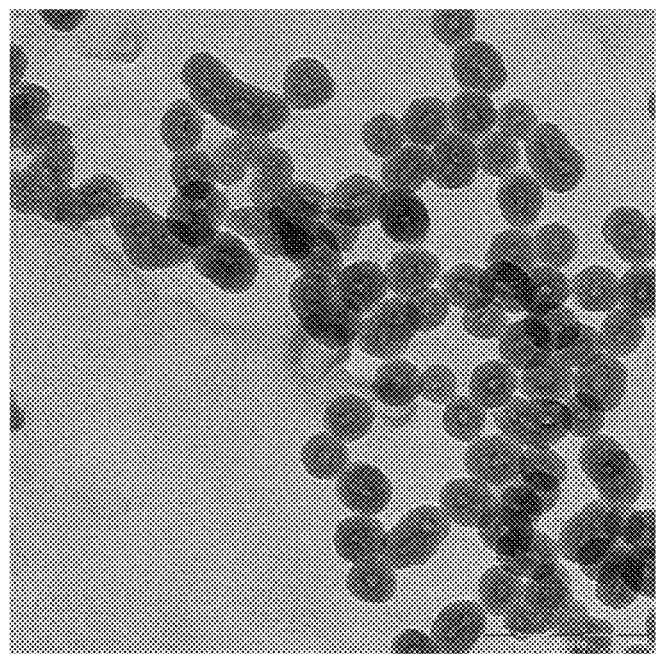
FIG. 1 shows the micrography obtained with a transmission electron microscope (TEM) for the hollow nanoparticles prepared as described in the following Example 3.

By "inorganic nanostructures" in the present invention inorganic nanoparticles are meant, having dimensions smaller than 3 nm, preferably selected from nanoparticles of superparamagnetic iron oxide, clusters of a metal selected from gold, silver and platinum, and mixtures of these clusters. According to a particularly preferred embodiment of the invention, the inorganic nanostructures comprised in the core of the present nanoparticles are clusters of gold.

The process for the preparation of silica hollow nanoparticles having in their cavity an aggregate of inorganic nanostructures according to the present invention comprises the following steps:

i) formation of ultra-small hydrophilic inorganic nanostructures, provided with a negatively charged coating, by reduction with sodium borohydride of an acid or of a salt of a metal in alcoholic solution;

ii) formation of an aggregate with poly(4-vinylpyridine) as an aggregating agent of the above said hydrophilic inorganic nanostructure, by addition of said poly(4-vinylpyridine) to an alcoholic solution of the inorganic nanostructures obtained from step i);

iii) formation of said silica hollow nanoparticles having in the cavity a metal core comprising the above said aggregate of hydrophilic inorganic nanostructures by hydrolysis of tetraethyl orthosilicate catalysed by ammonia in a mixture of ethanol and water in the presence of said aggregate as obtained from step ii).

In the nanostructures of this invention, the negatively charged coating is preferably created by a coating agent having carboxylic groups, more preferably by glutathione.

The glutathione or GSH, is a tripeptide formed by glycine, cysteine and glutamate, having well known anti-oxidant properties. It is a product already present in small amounts in the living organisms, where it mainly has a protective function of the cells from the free radicals. In recent years, thanks to its anti-oxidant properties, it was proposed as active component in several products such as supplements or drugs having antioxidant activity; it is therefore a completely acceptable product for use in products intended for ingestion with diagnostic or therapeutic purpose. Poly(4-vinylpyridine) is a product known to be safe and non-toxic too, and it is much used; preferably, in the present process poly(4-vinylpyridine) with average molecular weight of 60 kDa is used. The external hollow structure of the present nanoparticles, made of silica, protects the metal core from the external environment, this is perfectly biocompatible and biodegradable too, and it may be easily coated or functionalised with biomolecules. More in particular, the external surface of the present hollow nanoparticles can be easily modified and functionalised in the process of the present invention, and this can be achieved by means of standard protocols. The surface modification can be carried out with various polymers or peptides or salinising molecules, and preferably with (3-amino-propyl)triethoxysilane (APTES). Once modified, the surface can be on its turn functionalised with various biomolecules, for instance antibodies, aptamers, fluorophores, proteins, etc. selected based on the target towards which the nanoparticles have to be directed, by standard protocols, for instance by peptides chemistry techniques.

By the present process nanoparticles of defined size can be synthesised, consisting of a silica hollow nanostructure wherein inorganic nanostructures, aggregated among each other, are incorporated, taken together inside the cavity by the polymeric aggregating agent. The resulting structure, despite being complex and consisting of several components, is however extremely stable besides having a diameter smaller than 100 nm, able to reach the target tissues in a human body, to produce the desired diagnostic and/or therapeutic action, then to degrade and be excreted in the form of single components through the renal route.

In other words, for example from the optical point of view, the metal core of the present nanoparticles behaves as a unique body, but it is then degraded into the single components inside the organism for excretion or for particular functions, for example therapeutic functions, to which it may be intended for. The presence of the coating on the inorganic nanostructures and more in particular, when the coating agent is glutathione, of the two portions carboxylic acid of the glutathione molecule, can allow binding with pharmaceutical active principles, or prodrugs; the hollow nanoparticles of the invention can thus represent a controlled release system of the active principle in the organism, by degradation of the silica shell and release from the metal core once arrived on the target tissue.

The final structure of the hollow nanoparticles obtainable by the process of the invention ha a diameter smaller than 100 nm, and preferably comprised between 30 and 40 nm, while the metal clusters inside the cavity of these nanoparticles have each a diameter smaller than 3 nm, preferably comprised between 0.6 and 2 nm.

According to a particularly preferred embodiment of the invention, the nanoparticles are prepared by the present process with a diameter comprised between 30 and 40 nm, these dimensions being optimal for improving both the internalisation in the cells of tissues and the possibility to reach the target tissue.

These nanoparticles can be used as contrast agents, diagnostic and/or therapeutic agents, in imaging techniques in vivo, after administration in the human body, for example by enteral or preferably parenteral route. Within the body, after a certain period of time when nanoparticles are internalised into the cells of the target tissues, they are then degraded by releasing the single components, among which the metal clusters that, with their maximum size of 3 nm, can be eliminated without difficulties through the renal route. Examples of possible applications of this type for the present nanoparticles are in photoacoustics, or in radiotherapy.

The advantages of the process of the present invention are therefore multiple: first of all the process allows obtaining particles of much smaller size than the processes known for preparing similar particles. Furthermore, the present process allows obtaining nanoparticles that, once they have performed their action as diagnostic and/or therapeutic agent in the human body by interaction with cells and tissues, each particle as a unique body, they are degraded into the single components having such nature and dimensions as to be easily and rapidly eliminated through the renal route. Without wanting to be linked to a theory, inventors noted in particular that the presence of the glutathione molecules coating the metal clusters, together with their dimensions smaller than 3 nm, from the tests carried out, seems to influence excretion from the organism of the present nanoparticles that is completed in very short times.

The present process also allows, if desired, to obtain nanoparticles that can be functionalised on their external surface with several molecules, for example antibodies, aptamers, fluorophores, etc. by means of standard protocols. Moreover, ultra-small magnetic structures can be incorporated inside the cavity of the present nanoparticles when to form the metal core magnetic nanostructures are used, for example nanoparticles of superparamagnetic iron oxide (SuperParamagnetic Iron Oxide Nanoparticles, SPIONs). It is finally an extremely simple, low cost and reproducible process.

The nanoparticles obtainable by the present process can be subjected to lyophilisation and, in lyophilised form, be stored for a long time without losing their properties. Finally, they can be used for the biomedical applications described above, they also have optimal size for taking advantage of the so called effect of increased permeability and retention.

The following examples are provided as a non-limiting illustration of the present invention.

EXAMPLE 1

Synthesis of Metal Clusters

Gold clusters have been prepared according to the following procedure. To 50 ml of a methanol solution of $HAuCl_4.3H_2O$ (0.25 mmol, 0.1 g) 1.0 mmol (0.307 g) of glutathione was added. The mixture was then cooled under stirring in ice bath for 30 minutes up to the temperature of approximately 0° C. Then, under vigorous stirring, in this mixture have been rapidly injected 12.5 ml of a 0.2 M aqueous solution, freshly prepared, of sodium borohydride (0.1 g). The mixture was left to react for a further hour. The resulting precipitate was then harvested by centrifugation and washed for 3 times with methanol by centrifugation of the precipitate (each washing for 10 minutes at 13400 rpm) to remove the starting materials. Finally, the precipitate has been dissolved in water milliQ and lyophilised to yield 70 mg of gold clusters as a dark brown powder.

EXAMPLE 2

Synthesis of Aggregates of Metal Clusters 0.5 mg of gold clusters prepared as described above in the Example 1 were dissolved in 5 ml of ethanol, then 10 μl of a solution of poly(4-vinylpyridine) in dimethylformamide (60 kDa, 20 mg/ml in DMF) were added, maintaining under stirring for 30 minutes at room temperature. The so-obtained gold aggregates were collected by centrifugation (13400 rpm for 3 minutes), re-suspended in 400 ml of ethanol and subjected to sonication for maximum 4 minutes.

EXAMPLE 3

Synthesis of Hollow Nanoparticles Containing Aggregates of Metal Clusters

In a 100 ml round-bottom flask 35 ml of absolute ethanol, 1.2 ml of a 30% aqueous solution of ammonium hydroxide, and 20 μl of tetraethyl orthosilicate (TEOS, 98%) were poured. The so obtained reaction mixture was maintained for 20 minutes under stirring at room temperature, then 400 μl of the ethanol solution of gold aggregates prepared as described above in Example 2 were added with 1 ml of milliQ, and maintained under stirring for further 3 hours. Once stirring was stopped, the reaction mixture was centrifuged for 30 minutes at 4000 rpm to collect the nanoparticles formed, and then they have been washed twice with ethanol by centrifugation (each washings for 3 minutes at 13400 rpm) to remove the non-reacted precursors, and re-suspended in 1 ml of ethanol. The so obtained colloidal product was finally subjected to centrifugation at 13400 rpm for 5 minutes, re-suspended in 500 μl of water milliQ, subjected to sonication for 5 minutes and to lyophilisation overnight. It was thus obtained a pink powder that was stable for at least a year if stored in the dark at a temperature of 10° C.

EXAMPLE 4

Characterization of the Products Obtained in Examples 1-3

The silica hollow nanoparticles having aggregates of metal seeds in their cavity were analysed by Scanning Electron Microscopy (SEM) and by Transmission Electron Microscopy (TEM), as well as were analysed the intermediate products, i.e. the metal clusters and their aggregates with poly(4-vinylpyridine).

The TEM micrographies of the nanoparticles prepared as described above in the Example 3 are visible in FIG. 1. These analyses allowed checking the products actually formed in the process of the invention and showed, among other things, how the metal seeds in the form of aggregates, are completely internalised in the hollow spheres of silica.

Figure 2:
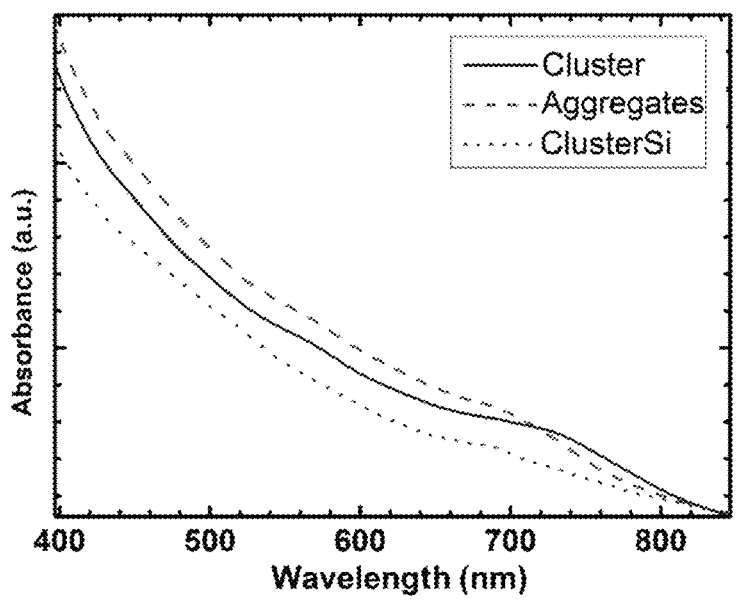
FIG. 2 shows the UV-Visible absorption spectra recorded for the products obtained in the following Examples 1-3, i.e. for the gold clusters of the Example 1 (—), for the aggregates with poly(4-vinylpyridine) 60 kDa of the Example 2 ( - - - ), and for the silica hollow nanoparticles with these aggregates of the Example 3 ( . . . ).

In FIG. 2 are depicted the UV-Visible absorption spectra recorded in a buffer solution in PBS 1× for the gold clusters, their aggregates and the nanoparticles containing them, prepared as described in Examples 1-3. Given the extremely small dimensions of the gold clusters, a very high percentage of metallic atoms is on the surface of the clusters themselves. This means that the ligands on their surface induce relevant modifications in their electronic and optical properties. As a matter of fact the spectrum of clusters in FIG. 2 (—) shows both a band that may be associated to plasmonic resonance (about 560 nm) and a band related to interband transitions of the metal centres (about 740 nm). After the aggregation with poly(4-vinylpyridine) ( - - - ) the band at 740 nm shifted to 700 nm. This could be ascribable to the ionic interaction between the GSH (negative) and the polymer (positive). The formation of the nanocapsules around the aggregates ( . . . ) seems to cause a further slight shift toward the blue of said band. In this case the effect might be linked to a lower scattering component on the spectrum.

The invention claimed is:

1. A process for the preparation of biodegradable silica hollow nanoparticles, having a diameter smaller than 100 nm and a metal core inside a cavity comprising inorganic nanostructures, each of said inorganic nanostructures having a diameter smaller than 3 nm and forming together an aggregate with poly(4-vinylpyridine), said process comprising:
   i) forming hydrophilic inorganic nanostructures having a diameter smaller than 3 nm, provided with a negatively charged coating, by reduction with sodium borohydride of an acid or a salt of a metal in alcoholic solution;
   ii) forming an aggregate with poly(4-vinylpyridine) as an aggregating agent of said hydrophilic inorganic nanostructure, by addition of said poly(4-vinylpyridine) to an alcoholic solution of the inorganic nanostructures obtained from step i); and
   iii) forming of said biodegradable silica hollow nanoparticles having in the cavity a metal core comprising said aggregate of hydrophilic inorganic nanostructures by hydrolysis of tetraethyl orthosilicate catalysed by ammonia in a mixture of ethanol and water in the presence of said aggregate as obtained from step ii).

2. The process according to claim 1, wherein said inorganic nanostructures are selected from among clusters of a metal selected from gold, silver and platinum, and mixtures of said clusters.

3. The process according to claim 2, wherein said metal is gold.

4. The process according to claim 1, wherein said biodegradable silica hollow nanoparticles have a diameter of between 30 and 40 nm, and said inorganic nanostructures have a diameter of between 1 and 2 nm.

5. The process according to claim 1, wherein said coating of the inorganic nanostructures is formed by a coating agent provided with carboxylic acid groups.

6. The process according to claim 5, wherein said coating agent is glutathione.

7. The process according to claim 1, wherein said inorganic nanostructures coming from step i) are subject to functionalization of the coating with one or more functional molecules having pharmacological activity before being aggregated in the subsequent step ii).

8. The process according to claim 1, further comprising modifying and/or functionalizing the outer surface of said silica nanoparticles with one or more molecules, selected from the group consisting of antibodies, aptamers, fluorophores, proteins, polymers and silanising peptides.

9. The process according to claim 1, further comprising lyophilizing of the silica nanoparticles obtained from step iii).

10. An intermediate in the process for the preparation of nanoparticles as defined in claim 1, consisting of an aggregate of inorganic nanostructures with a negatively charged coating, each having a diameter smaller than 3 nm and forming together an aggregate with poly(4-vinylpyridine).

11. The intermediate as defined in claim 10, for the preparation of biodegradable silica hollow nanoparticles with a metal core inside their cavity comprising inorganic nanostructures in the form of an aggregate.

12. Biodegradable hollow silica nanoparticles obtained by the process of claim 1, having a diameter smaller than 100 nm and a metal core inside their cavity comprising inorganic nanostructures with a negatively charged coating, each having a diameter smaller than 3 nm and forming together an aggregate with poly(4-vinylpyridine).

13. The nanoparticles according to claim 12, having a diameter ranging between 30 and 40 nm and comprising in the core inside their cavity inorganic nanostructures each of dimensions ranging between 1 and 2 nm.

14. The intermediate of claim 10, wherein said inorganic nanostructures are clusters of gold.

15. A diagnostic and/or therapeutic agent suitable for administration by enteral or parenteral route into the human body for bioimaging techniques and/or for radio-therapy or chemo-therapy techniques comprising the nanoparticles of claim 12.

16. The nanoparticles of claim 12, wherein said inorganic nanostructures are clusters of gold.

17. The process according to claim 1, further comprising incorporating nanoparticles of superparamagnetic iron oxide inside said cavity.

* * * * *